United States Patent
Singhal

(10) Patent No.: US 9,855,311 B2
(45) Date of Patent: *Jan. 2, 2018

(54) PACKAGING OF HERBAL COMPOUND FORMULATIONS AS DIETARY SUPPLEMENTS

(76) Inventor: Tara Chand Singhal, Torrance, CA (US)

( * ) Notice: Subject to any disclaimer, the term of this patent is extended or adjusted under 35 U.S.C. 154(b) by 1315 days.

This patent is subject to a terminal disclaimer.

(21) Appl. No.: 13/429,388

(22) Filed: Mar. 25, 2012

(65) Prior Publication Data

US 2012/0181206 A1    Jul. 19, 2012

Related U.S. Application Data

(62) Division of application No. 12/383,175, filed on Mar. 20, 2009.

(60) Provisional application No. 61/123,261, filed on Apr. 7, 2008.

(51) Int. Cl.
| | |
|---|---|
| *A61K 36/53* | (2006.01) |
| *A61K 36/756* | (2006.01) |
| *A61K 36/9066* | (2006.01) |
| *A61K 36/185* | (2006.01) |
| *A61K 36/534* | (2006.01) |
| *A61K 36/47* | (2006.01) |

(52) U.S. Cl.
CPC .......... *A61K 36/9066* (2013.01); *A61K 36/47* (2013.01); *A61K 36/53* (2013.01)

(58) Field of Classification Search
CPC .............................. A61K 36/53; A61K 36/9066
USPC .................................................. 424/725, 756
See application file for complete search history.

(56) References Cited

U.S. PATENT DOCUMENTS

| | | | | |
|---|---|---|---|---|
| 2003/0185913 A1* | 10/2003 | Pushpangadan | ...... | A23L 1/3002 424/739 |
| 2004/0103908 A1* | 6/2004 | Prakash | ................. | A24B 15/16 131/359 |
| 2006/0263750 A1* | 11/2006 | Gordon | .............. | G09B 19/0092 434/127 |
| 2009/0071857 A1* | 3/2009 | Astwood | ................. | G09F 23/00 206/459.5 |
| 2011/0159118 A1* | 6/2011 | Patell | ..................... | G01N 33/94 424/725 |

FOREIGN PATENT DOCUMENTS

| | | | |
|---|---|---|---|
| IN | 188649 B | * | 10/2002 |
| IN | 191247 B | * | 10/2003 |
| IN | 200000459 | * | 3/2005 |
| IN | 20000018613 | * | 8/2005 |
| IN | 200500744 | * | 3/2006 |
| JP | 2005325025 A | * | 11/2005 |
| WO | WO 0054794 A1 | * | 9/2000 |

\* cited by examiner

*Primary Examiner* — Chris R Tate
(74) *Attorney, Agent, or Firm* — Steve Roeder Esq.

(57) ABSTRACT

Herbal compound formulations using herbs *curcuma longa* (turmeric), *ocimum sanctum* (holy basil) and *emblica officinalis* (amla) in their natural forms and a method of packaging the same for dietary supplement as tablets, wafers, capsules and as teabags where the packaging of individual dosages and the outer packaging may use visual display of color that represents the proportion and presence of different herbs in the herbal compound.

18 Claims, 2 Drawing Sheets

PACKAGING OF HERBAL COMPOUND FORMULATIONS AS DIETARY SUPPLEMENTS

CROSS REFERENCE

This application is a divisional of U.S. application Ser. No. 12/383,175, filed Mar. 20, 2009, titled "*Curcuma Longa* (Turmeric) Based Herbal Compound Formulations as Dietary Supplements" of Tara Chand Singhal.

This application claims priority on Provisional Application Ser. No. U.S. 61/123,261, Titled "*Curcuma Longa* (Turmeric) Based Herbal Compound Formulations As Dietary Supplements," Filed On Apr. 7, 2008, By Tara Chand Singhal. The Contents of the Provisional Application Ser. No. 61/123,261 are incorporated herein by reference.

FIELD OF THE INVENTION

Herbal compound formulations that use herbs *curcuma longa* (turmeric), *ocimum sanctum* (holy basil) and *emblica officinalis* (amlaki) in their natural forms and packaging of the same that visually highlights their health benefits as dietary supplement are described.

BACKGROUND

Turmeric herb is widely known and has been widely researched in both the western world and in India for its many health benefits. Turmeric extracts are being planned for use in many modern medicines and have been used in Auyervedic medicines and personal care products. Amlaki herb is not as widely known as Turmeric to the western world, but it has been researched for its health properties in the Indian sub-continent. Tulsi, also known as Holy Basil, is much less known to the western world compared to Turmeric, even though it has also been researched in the India for its health properties. The primary use of Tulsi in India is for religious purposes. Hence, each of these herbs has been well researched for their health and desirable medicinal properties and effect on human health on both in their preventive and curative properties.

Individually, these Indian herbs, Tulsi, Amlaki, and Turmeric have many beneficial health properties as highlighted from the wikipedia and other references on the Internet, below:

Tulasi's extracts are used in ayurvedic remedies for common colds, headaches, stomach disorders, inflammation, heart disease, various forms of poisoning, and malaria. Studies have also shown Tulsi to be effective for diabetes, by reducing blood glucose levels. The same study showed significant reduction in total cholesterol levels with Tulsi. Another study showed that Tulsi's beneficial effect on blood glucose levels is due to its antioxidant properties.

In some literature, Tulsi is also known as Holy Basil. Holy Basil herb has been used for centuries to treat a variety of medical conditions including heart problems, asthma, bronchitis, and arthritis and eye disorders. In the past decade, a number of scientific studies have looked at Holy Basil for various treatment purposes. Findings from these various investigations have suggested that Holy Basil might be useful as a stress-reducer, painkiller, anti-inflammatory agent, an antioxidant, and as a treatment for bacterial, fungal and even viral infections. Holy Basil is also taken for reducing both stress and elevated levels of the stress hormone cortisol, and to promote physical and emotional endurance.

Holy Basil is also famous as an herb that promotes optimum respiratory support. Its expectorant properties are useful in promoting a healthy respiratory system. Holy Basil, called "the incomparable one" is very important in Indian folk medicine. It is characterized by strong aroma. It belongs to the Rasayana herbs category that supports normal function of the whole body. The phytonutrients within Holy Basil are prized molecules in the plant pharmacy. It contains eugenol linalool, ursolic acid, calcium, vitamin C, carotene, phosphates.

Amlaki, an Indian gooseberry, has undergone preliminary research, demonstrating in vitro antiviral and antimicrobial properties. Experimental preparations of leaves, bark or fruit have shown potential efficacy against laboratory models of disease, such as for inflammation, cancer, age-related renal disease, and diabetes.

Although fruits are reputed to contain high amounts of ascorbic acid (vitamin C), the specific contents are disputed and the overall antioxidant strength of amla may derive instead from its high density of tannins and other polyphenols. The fruit also contains flavonoids, kaempferol, ellagic acid and gallic acid.

Amla also know as Amlaki in some literature or *Emblica Officinalis* is a natural, efficacious, an antioxidant with the richest natural source of Vitamin C. The fruit contains the highest amount of Vitamin C in natural form and cytokine like substances identified as zeatin, z. riboside, z. nucleotide. Its fruit is acrid, cooling, refrigerant, diuretic and laxative. The dried fruit is useful in hemorrhage, diarrhea and dysentery. It is antibacterial and its astringent properties prevent infection and help in the healing of ulcers. It is used as a laxative to relieve constipation in piles. It is used in the treatment of leukorrhea and atherosclerosis.

Amalaki is referred to in ancient text as the best medicine to prevent aging. It is a very strong rejuvenative which is believed to be the richest natural source of antioxidant vitamin C, with up to 720 mg/100 g of fresh pulp or up to 900 mg/100 g of pressed juice (of a heat-stable form which does not lose its value through processing.) Although only one inch in diameter, the Amalaki fruit has the same anti-scorbutic value as two oranges. Amalaki is also effective for respiratory complaints. The fruit juice and its sediment, and residue, have antioxidant properties due to Vitamin C content. Amalaki is a carminative and stomachic. It is used in Ayurveda as a cardiotonic, aphrodisiac, antipyretic, antidiabetic, cerebral and gastrointestinal tonic. It raises the total protein level and increases the body weight due to positive nitrogen balance. It has been found to have an anabolic effect.

Amla is highly nutritious and is an important dietary source of Vitamin C, minerals and amino acids. The edible fruit tissue contains protein concentration 3-fold and ascorbic acid concentration 160-fold compared to that of the apple. The fruit also contains considerably higher concentration of most minerals and amino acids than apples. Amla fruit ash contains chromium, 2.5; zinc, 4; and copper, 3 ppm. Presence of chromium is of therapeutic value in diabetes. Fruit also contains phyllemblin and curcuminoides. The fruit contained 482.14 units of superoxide dismutase/g fresh weight, and exhibited antisenescent activity. Not surprisingly, Amla's reputation is supported by scientific studies confirming its immunity-boosting properties.

In Ayurvedic medicine, Turmeric is thought to have many medicinal properties and many in India use it as a readily available antiseptic for cuts, burns and bruises. Practitioners of Ayurvedic medicine say it has fluoride which is thought to be essential for teeth. It is also used as an antibacterial agent.

It is only in recent years that Western scientists have increasingly recognized the medicinal properties of turmeric. According to a 2005 article in the Wall Street Journal titled, "Common Indian Spice Stirs Hope," research activity into curcumin, the active ingredient in turmeric, is exploding. Two hundred and fifty-six curcumin papers were published in the past year according to a search of the U.S. National Library of Medicine. Supplement sales have increased 35% from 2004, and the U.S. National Institutes of Health has four clinical trials underway to study curcumin treatment for pancreatic cancer, multiple myeloma, Alzheimer's, and colorectal cancer.

"Curcumin has been used for thousands of years as a safe anti-inflammatory in a variety of ailments as part of Indian traditional medicine," Gregory Cole, Professor of medicine and neurology at the David Geffen School of Medicine at UCLA said. Anti-tumoral effects against melanoma cells have been demonstrated.

Curcumin is thought to be a powerful antinociceptive (pain-relieving) agent. In the November 2006 issue of *Arthritis & Rheumatism*, a study was published that showed the effectiveness of turmeric in the reduction of joint inflammation, and recommended clinical trials as a possible treatment for the alleviation of arthritis symptoms. It is thought to work as a natural inhibitor of the cox-2 enzyme, and has been shown effective in animal models for neuropathic pain secondary to diabetes, among others.

There are many health benefits of turmeric. These benefits also come from curcumin, which is an ingredient in turmeric. Turmeric is the spice from India that is used in curry dishes. Curcumin is the part of turmeric that gives curry food its golden color. This also provides turmeric with curcuminoids, which are believed to have health properties such as antioxidant, antibacterial and anti-inflammatory qualities.

Turmeric is known to have anti-inflammatory effects, so it may be used to treat arthritis and other inflammatory conditions. In recent studies, curcumin (also known as diferuloylmethane)—one of the active chemicals contained in turmeric—has been found to limit the activity of several chemicals including two enzymes, lipoxygenase and cyclooxygenase-2 (COX-2), that are involved in promoting and maintaining inflammation. By reducing the effects of these enzymes, curcumin may also reduce inflammation and the pain associated with it in conditions such as arthritis.

As a flavoring, turmeric is consumed in varying—often-large—amounts by individuals of all ages. In clinical studies of humans, oral doses of turmeric ranged from about 500 mg (0.5 gram) to several grams per day. Although most doses were less than half of large, one-time doses of 12,000 mg (12 grams) and daily oral doses of up to 8,000 mg (8 grams) of turmeric for as long as 3 months produced no apparent side effects for the individuals who took them (drugdigest.com).

The prior art as summarized above is largely focused on chemically analyzing and extracting beneficial chemical substances from these herbs and using such extracts to individually combine with existing medicines and health preparations for purposes such as skin ointment, hair treatments, eye drops and combined with western medications such as for diabetes and Alzheimer. Herbal dietary supplement companies also package each of these herbs separately in capsule form as dietary supplements.

It is the objective of this preferred embodiment that, given the widely researched multiple benefits of these herbs individually, compound formulations of these herbs would be highly beneficial for optimum health for those whose dietary intake does not use these specific herbs.

SUMMARY

The focus of this preferred embodiment is to use these three specific herbs of amlaki, holy basil and turmeric in their natural herbal form in an herbal compound, as they have shown to have many types and levels of benefits to human health, as summarized below and described in some detail in the background section. Hence, the herbal compound formulations of this preferred embodiment combine these three specific herbs in certain proportions rather than extract specific chemicals from them, the effort of western medical science.

Amlaki, an Indian gooseberry has been treasured in India for over 5,000 years for its restorative and balancing influences on the body. It is the richest natural source of vitamin 'C'. The amount of vitamin 'C' in amlaki is four times more than it is in oranges and eight times more than it is in tomatoes. It is so rich that the vitamin doesn't get destroyed whether you burn or dry it. Amlaki is known as a rasayana (having restorative and balancing effects on the three constitutional elements that govern human life: Vat, Pit and Kaph.

In India, the herb tulsi also called holy basil (sometimes spelled "tulasi") has been widely known for its health promoting and medicinal value for thousands of years. Commonly called sacred or holy basil, it is a principal herb of Ayurveda, the ancient traditional holistic health system of India. Holy basil is known as "The Incomparable One", "The Mother Medicine of Nature", and "The Queen of Herbs". Holy Basil should not be confused with sweet basil herb that is commonly used in western cooking.

Turmeric, a member of the ginger family, has been used for healing by Ayurvedic means, since time immemorial. Turmeric has anti-inflammatory properties, and is an excellent antiseptic. In addition, it is great for the skin.

It is believed, the herbal formulations of this preferred embodiment would supply the benefits of these herbs, long used separately for different purposes in the Indian continent, such as in diet and in medical products, to the entire world, and specifically the western world, where the dietary intake does not include these herbs and where these herbs are not easily available. Three herbal compounds, each with turmeric as the primary herbal ingredient are described. One of these herbal formulations has turmeric with amla and holy tulsi, another formulation has turmeric with amla and a third formulation has turmeric with tulsi.

Further in this preferred embodiment, to create a positive mental impression for those who would take these herbal compound formulations, when taking these specific compounds, these herbal compounds may be packaged in a form with a visual display of the proportion of the ingredients in the form. The visual display may use color that corresponds substantially to the color of the ingredients. For example, that is yellow for turmeric, light green for amlaki and dark green for tulsi, thus visually and mentally reinforcing their health benefits each time the dosage is taken.

BRIEF DESCRIPTION OF THE DRAWINGS

Some of the novel features of this preferred embodiment will be best understood from the accompanying drawings, taken in conjunction with the accompanying description, in which similar reference characters refer to similar parts, and in which.

DESCRIPTION

Figure 1:
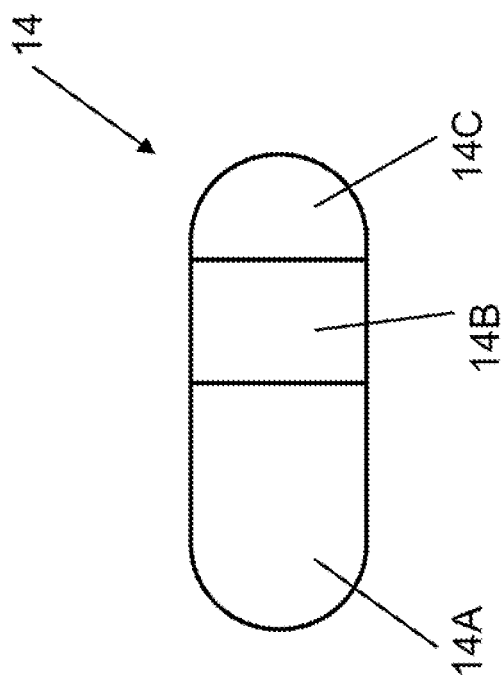
FIG. 1 is a block diagram that illustrates features of the present preferred embodiment of visual display of ingredients on the dose in the form of tablet, capsule and wafer.
Figure 1:
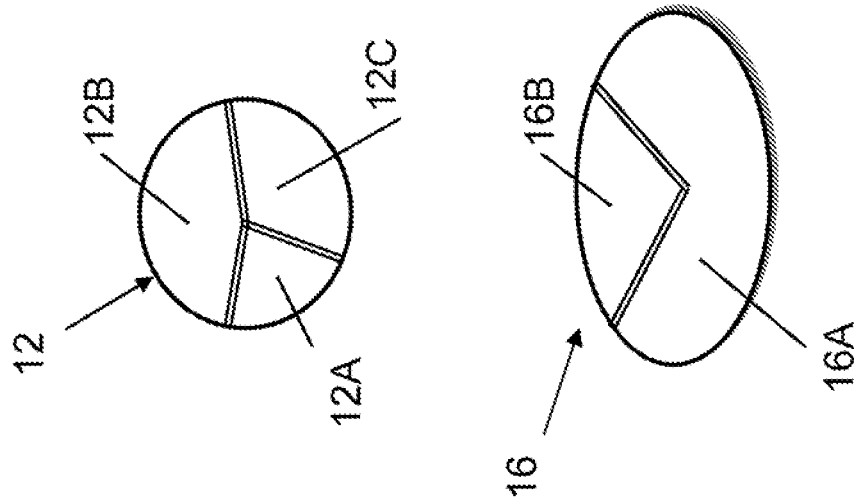

The present preferred embodiment is directed to herbal compound formulations for achieving and maintaining optimum human health. The herbal compound formulation named TURBAAM™, has a proportion of herb *ocimum sanctum* (Indian holy tulsi); a proportion of herb *emblica officinalis* (Indian gooseberry amlaki); and a proportion of herb *curcuma longa* (turmeric), wherein the compound is formulated in a form that is suitable for human consumption as a dietary supplement.

The herbal compound formulation TURBAAM has as the proportion of *ocimum sanctum* herb (tulsi), by weight that is not below 9.5% and not greater than 25.5%; the proportion of *emblica officinalis* herb (amlaki), by weight that is not below 19.5%, and not greater than 35.5%; and the proportion of *curcuma longa* herb (turmeric), by weight that is not below 49.5% and not greater than 70.5% in the herbal compound.

These percentage ranges take into account the properties of these specific individual herbs as they naturally occur and their use in Ayervedic medicines. Holy tulsi herb is available in the form of leaves. Amlaki is available in the form of a goose berry. Turmeric is available in the form of a rhizome root. The percentage ranges also take into account in how they are used in diet and as health supplements. These percentage ranges are believed more efficacious for human health as dietary supplement in these proportions.

As a simplified illustration, a dose formulated in the weight of 1000 milligram (mg) may have tulsi as 100 mg., amlaki as 300 mg., and turmeric as 600 mg, making tulsi as 10%, that is between 9.5% and 25.5%, making amlaki as 30%, that is between 19.5% and 35.5%, and making turmeric as 60%, that is between 49.5% and 70.5% by weight.

As another illustration, a dose formulated as a wafer of 6 grams, may have tulsi as 1 gram or 16.7%, amlaki as 2 gram or 33% and turmeric as 3 gram or 50% by weight. All variations and dosages are possible with in the limits of dosage and proportions as described here.

Alternatively, an herbal compound, named TURBA for human health may have a formulation of a proportion of *ocimum sanctum* (holy tulsi) with a proportion of *curcuma longa* (turmeric), where the compound is formulated in a form for human consumption.

The proportions in the herbal compound TURBA may be the proportion of *ocimum sanctum*, by weight is not below 19.5% and does not exceed 49.5% with the proportion of *curcuma longa* by weight is not below 49.5% and does not exceed 80.5%, where the compound is formulated in a form for human consumption.

Alternatively, an herbal compound, named TURAM, for human health may have a formulation of a proportion of *emblica officinalis* (Indian gooseberry amlaki), with a proportion of *curcuma longa* (turmeric), where the compound is formulated in a form for human consumption.

The proportion in the herbal compound, TURAM, may be the proportion of *emblica officinalis* by weight is not below 29.5% and does not exceed 50.5% with the proportion of *curcuma longa* (Turmeric) by weight is not below 49.5% and does not to exceed 70.5%, where the compound is formulated in a form for human consumption.

The herbal compounds as described above use natural form of these individual herbs. For, turmeric, powder form of the root may be used. For Tulsi, which are leaves, powder form dried leaves may be used. For, amlaki, a berry, dried and powdered form of the berry fruit may be used.

The herbal compound may use a natural binding agent. For example, gum karaya is a natural edible gum derived from the secretions of karaya tree. Other binding agents may also be used.

The herbal compounds may be formulated in form such as a liquid dissolvable wafer, a capsule, or a tablet or a tea bag in single doses. If the packaging is in the form of a tablet or wafer or capsule, suitable coating agents may be used. Vegetable based coatings are preferred over animal based coatings.

Methocel from Dow is a vegetable based coating, as describe on the web site for Dow Excipients. METHOCEL. Premium cellulose ethers offer an excellent combination of properties for water-soluble hard shell capsules. Among their long list of advantages, perhaps one of the most important is that METHOCEL polymers are of plant origin. Compared to animal-based gelatin, this allows them to satisfy many specific cultural and religious needs, while at the same time delivering superior and more uniform performance.

The herbal compound may also use a flavoring agent in the compound itself or the coating as appropriate. The flavoring that is preferred is using one of from cinnamon oil, cardamom oil, and peppermint oil, which may be used with the ingredients or may be used with the coating as appropriate. These specific types of flavorings would appeal to a large population in different countries. These are commonly used natural form derived flavorings in food.

Western medical research has shown over many decades that placebo plays a large positive role in human health, where as much as 30% to 60% of the patients are healed by placebos in double blind controlled medical trials. This shows that the belief of the humans in the efficacy of the drug is a consistently large, important and undeniable factor.

Therefore, to create a positive mental impression on humans when taking these herbal compounds, and to beneficially realize the benefit of such placebo effect, these herbal compounds may be packaged in a form with a visual display of the proportion of the ingredients in the form. The form may be a wafer, a capsule, a tablet, or a teabag.

The health benefits of each of these individual herbs are well known and can be described on the packaging. The user when ingesting the single dose herbal formulations of this preferred embodiment, the user would know through the visual display that he is ingesting these herbs directly. Hence when taking these herbal compounds of this preferred embodiment, in any of these forms, the user would know actually what he is taking and what quantity and proportion he is taking that in.

The visual display may take any number of forms such as, name/symbol of the ingredient in the herbal compound formulation and/or the color of the ingredients on the tablet or capsule. The color is preferred embodiment as it can be easily applied to the outer covering or coating of the capsule, the tablet, and the wafer forms of the herbal compound. Also the color acts as a powerful and immediate mental and visual impression of the quantity and proportion of the herbal ingredients in the herbal compound.

The color may be applied to either the tablet itself, or the packaging or both. Each dosage may be individually packaged. For example when the herbal compound is packaged as tea bag, it may be the tea bag packaging. When the compound is formulated as a capsule, wafer, each capsule or the wafer may be individually packaged.

The visual display may use color that corresponds substantially to the color of the ingredients, for example, that is yellow for turmeric, light green for amlaki and dark green for holy basil. The color of these herbs would be known to the user. Hence each time, he/she takes the herbal compound so packaged as in this preferred embodiment, he/she would be impressed with the knowledge he/she is taking the herbal compound that gives them so much of turmeric and so much amla and so much of the tulsi in its natural form.

The packaging for an herbal compound formulation may visually show a proportional sector forming an ingredient A, a proportional sector forming an ingredient B, and a proportional sector forming a third ingredient, where the combination of the sectors forms a closed figure. The closed figure may substantially be a circle or a multisided figure or an oval of a wafer tablet, and each sector has color that corresponds to the color of the ingredient. Furthermore, the form that may be in capsule, tablet etc. or wafer may further be individually packaged in a package that displays the identical ingredient colors of the form such as wafer tablet.

As a simplified illustration as shown in FIG. 1, if the herbal compound is in the shape of a circular wafer tablet 12, the proportion of turmeric is shown by sector 12B, amla by sector 12C and tulsi by sector 12A. If the herbal compound is in the shape of an oval tablet 16, the proportion of turmeric may be shown by sector 16A and amla by sector 16B. If the herbal compound is packaged as a capsule 14, the proportion of turmeric may be shown by color band 14A, the proportion of amlaki may be shown by color band 14B, and the proportion of tulsi or holy basil may be shown by color band 14C.

Figure 2B:
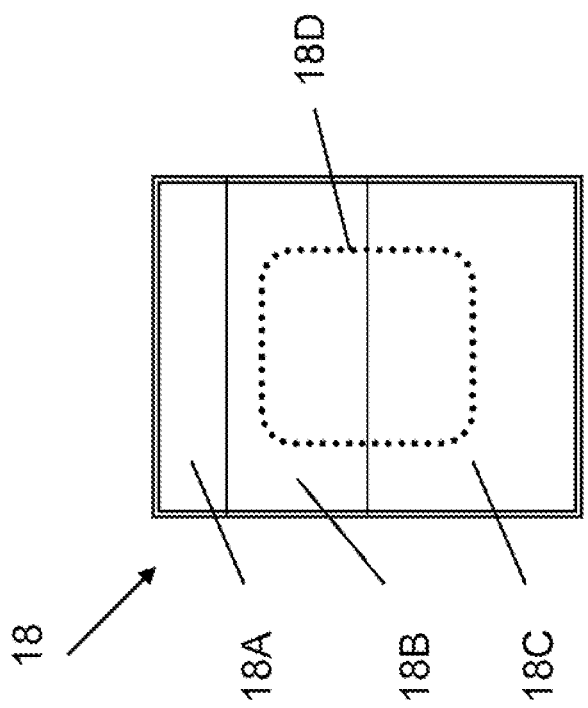
FIG. 2B is a block diagram that illustrates features of the present preferred embodiment of visual display of ingredients on the dose as a tea bag packaging.
Figure 2A:
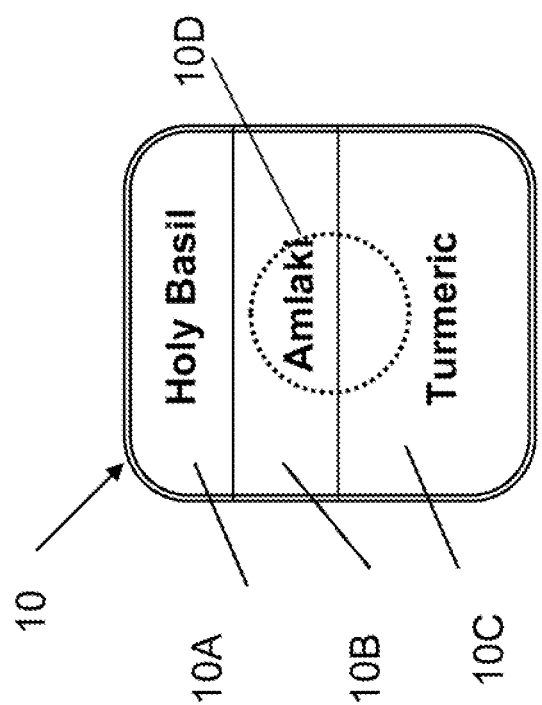
FIG. 2A is a block diagram that illustrates features of the present preferred embodiment of visual display of ingredients on the dose packaging.

As shown in FIG. 2A, if the herbal compound dose is packaged as individual dose, of a wafer tablet 10D or even a capsule inside a packaging 10, the proportion of turmeric may be shown by name and color sector 10C, the proportion of amlaki by name and color sector 10B and proportion of holy basil by name and color sector 10A on the individual packaging 10.

As shown in FIG. 2B, if the herbal compound is packaged as a tea bag 18D inside a packaging bag 18, the proportion of turmeric may be shown by color sector 18C, the proportion of amlaki by color sector 18B and proportion of holy basil by color sector 18A on the individual packaging 18.

The shapes, sizes and coloring of the tablets and capsule is a prior art as is commonly used by many companies that manufacture drugs and supplements. Hence no specific claim is made to any manufacturing process for producing these forms of packaging of doses. What this preferred embodiment claims is the visual display on these forms of the proportion of the ingredients that can be identified by color or symbols or words.

The packaging for an herbal compound may also have a visual display of the proportion of herbal ingredients in the herbal compound by use of color on the outer covering of the packaging of multiple doses of the compound, where each color represents the color of the ingredient herb and the proportion of that herb in the dose.

The herbal compound may be formulated for an individual dose for human consumption in the weight range of 375 mg. to 8.00 gram. Or it may be consumed in multiple doses in a day. The larger size of 8 grams may be suitable for a single dose/per day use and smaller sized may be used for multiple doses per day.

The size of 8 g/day is known to cause no harm and is similar to what is used in cooking, based on drugdigest.com information for *curcuma longa*. For illustration, in an 8 g. packaging, the turmeric may be 5 gram, the amla may be 2 gram and the tulsi may be one gram. Or any other proportion may be used, with at least 9.5% for tulsi and 19.5% amla and 49.5% for turmeric. For other formulations that use turmeric and either tulsi or amlaki, the turmeric may be 6 gram and the other may be 2 gram.

In summary, the preferred embodiment is on herbal compounds and packaging of the same as dietary supplements as these herbal compounds using turmeric, amlaki and tulsi are not part of the dietary intake of western world and rest of the world. The packaging of the herbal compounds in individual doses visually illustrates in single doses the ingredients present in these herbal compounds.

While the particular preferred embodiment, as illustrated herein and disclosed in detail is fully capable of obtaining the objective and providing the advantages herein before stated, it is to be understood that it is merely illustrative of the presently preferred embodiments of the invention and that no limitations are intended to the details of construction or design herein shown other than as described in the appended claims.

What is claimed is:

1. A package containing an herbal formulation, wherein at least one herb ingredient within the herbal formulation is a plant or plant part valued for its medicinal qualities, the package comprising a single-dose of the herbal formulation;
    wherein the herbal formulation is in a form selected from the group consisting of a wafer, a capsule, a tablet, and a teabag;
    wherein the herbal formulation comprises at least two herb ingredients selected from the group consisting of the herb *Curcuma longa*, the herb *Emblica officinalis*, and the herb *Ocimum sanctum*;
    wherein an outside surface of the package comprises a visual display showing the relative proportions of the herb ingredients in the herbal formulation, wherein each of the herb ingredients is represented as a segment within a multi-segmented figure, and wherein the visual display creates a mental impression of the medicinal benefits of the herbal formulation on a user of the herbal formulation.

2. The package according to claim 1, wherein the segments in the multi-segmented figure display a representation of the proportions of the herb ingredients in the herbal formulation by one of: a color for each of the herb ingredients, an identification for each of the herbal ingredients by name/symbol, or by both color and name/symbol.

3. The package according to claim 1, wherein the proportions of the herbal ingredients are by weight.

4. The package according to claim 1, wherein the segments within the multi-segmented figure substantially forms a closed figure in the form of a circle or a multi-sided figure.

5. The package according to claim 1, wherein the herbal formulation is in the form of a wafer.

6. The package according to claim 1, wherein the herbal formulation is in the form of a tablet.

7. The package according to claim 1, wherein the herbal formulation is in the form of a capsule.

8. The package according to claim 1, wherein the herbal formulation is in the form of a teabag.

9. A multi-dose package containing multiple numbers of the single-dose package according to claim 1, wherein an outer surface of the multi-dose package also comprises a visual display showing the relative proportions of the herb ingredients in the herbal formulation, wherein each of the herb ingredients is represented as a segment within a multi-segmented figure, and wherein the visual display creates a mental impression of the medicinal benefits of the herbal formulation on a user of the herbal formulation.

10. A method for preparing a single-dose package containing an herbal formulation comprising the steps of:
providing a single-dose package, and
adding an herbal formulation to the single-dose package;
wherein at least one herb ingredient within the herbal formulation is a plant or plant part valued for its medicinal qualities;
wherein the herbal formulation is in a form selected from the group consisting of a wafer, a capsule, a tablet, and a teabag;
wherein the herbal formulation comprises at least two herb ingredients selected from the group consisting of the herb *Curcuma longa*, the herb *Emblica officinalis*, and the herb *Ocimum sanctum;*
wherein an outside surface of the package comprises a visual display showing the relative proportions of the herb ingredients in the herbal formulation, wherein each of the herb ingredients is represented as a segment within a multi-segmented figure, and wherein the visual display creates a mental impression of the medicinal benefits of the herbal formulation on a user of the herbal formulation.

11. The method according to claim 10, wherein the segments in the multi-segmented figure display a representation of the proportions of the herb ingredients in the herbal formulation by one of: a color for each of the herb ingredients, an identification for each of the herbal ingredients by name/symbol, or by both color and name/symbol.

12. The method according to claim 10, wherein the proportions of the herbal ingredients are by weight.

13. The method according to claim 10, wherein the segments within the multi-segmented figure substantially forms a closed figure in the form of a circle or a multi-sided figure.

14. The method according to claim 10, wherein the herbal formulation is in the form of a wafer.

15. The method according to claim 10, wherein the herbal formulation is in the form of a tablet.

16. The method according to claim 10, wherein the herbal formulation is in the form of a capsule.

17. The method according to claim 10, wherein the herbal formulation is in the form of a teabag.

18. The method according to claim 10, further comprising the step of incorporating multiple numbers of the single-dose package into a multi-dose package, wherein an outer surface of the multi-dose package also comprises a visual display showing the relative proportions of the herb ingredients in the herbal formulation, wherein each of the herb ingredients is represented as a segment within a multi-segmented figure, and wherein the visual display creates a mental impression of the medicinal benefits of the herbal formulation on a user of the herbal formulation.

* * * * *